United States Patent
Huang et al.

(10) Patent No.: US 10,157,483 B2
(45) Date of Patent: Dec. 18, 2018

(54) BACKPROJECTION APPROACH FOR PHOTOACOUSTIC IMAGE RECONSTRUCTION

(71) Applicants: He Huang, San Antonio, TX (US);
Jing Yong Ye, San Antonio, TX (US)

(72) Inventors: He Huang, San Antonio, TX (US);
Jing Yong Ye, San Antonio, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 754 days.

(21) Appl. No.: 14/577,960

(22) Filed: Dec. 19, 2014

(65) Prior Publication Data
US 2015/0178959 A1 Jun. 25, 2015

Related U.S. Application Data

(60) Provisional application No. 61/918,365, filed on Dec. 19, 2013.

(51) Int. Cl.
*A61B 5/05* (2006.01)
*G06T 11/00* (2006.01)
*A61B 5/00* (2006.01)

(52) U.S. Cl.
CPC ......... *G06T 11/006* (2013.01); *A61B 5/0095* (2013.01); *G06T 2211/421* (2013.01)

(58) Field of Classification Search
CPC ............... A61B 5/0095; G06T 11/006; G06T 2211/421
See application file for complete search history.

(56) References Cited

U.S. PATENT DOCUMENTS

| 2013/0190595 A1* | 7/2013 | Oraevsky | A61B 5/0095 600/407 |
| 2014/0029819 A1* | 1/2014 | Zeng | G06T 11/003 382/131 |

OTHER PUBLICATIONS

R. A. Kruger, et al., "Photoacoustic Ultrasound (Paus)—Reconstruction Tomography," Medical Physics, vol. 22, pp. 1605-1609, Oct. 1995.

(Continued)

*Primary Examiner* — Mark Remaly
(74) *Attorney, Agent, or Firm* — Thomas | Horstemeyer, LLP

(57) ABSTRACT

Various examples are provided for photoacoustic image reconstruction and processing utilizing a backprojection approach. In one example, among others, a method for producing an image with a photoacoustic imaging system includes scanning an object with a plurality of light beams, detecting a plurality of acoustic signals produced by the light beams, and generating a reconstructed image from the plurality of acoustic signals by filtered backprojection (FBP) that utilizes a weighted ramp filter. In another example, a system includes a plurality of acoustic detector units and a processing unit. The acoustic detector units can receive an acoustic wave and convert it to time dependent electrical signals. The processing unit can reconstruct an image of the subject from the time-dependent electrical signals by FBP that utilizes a weighted ramp filter. In another example, non-transitory computer readable medium stores a program that can cause a processing unit to reconstruct an image.

12 Claims, 14 Drawing Sheets

(56) References Cited

OTHER PUBLICATIONS

P. Beard, "Biomedical photoacoustic imaging," Interface Focus, vol. 1, pp. 602-631, Aug. 6, 2011.
A. A. Oraevsky, et al., "Two-dimensional opto-acoustic tomography transducer array and image reconstruction algorithm," Proc. SPIE, vol. 3601, pp. 256-267, 1999.
M. H. Xu and L. H. V. Wang, "Universal back-projection algorithm for photoacoustic computed tomography," Physical Review E, vol. 71, Jan. 2005.
L. A. Kunyansky, "A series solution and a fast algorithm for the inversion of the spherical mean Radon transform," Inverse Problems, vol. 23, pp. S11-S20, Dec. 2007.
P. Kuchment and L. Kunyansky, "Mathematics of photoacoustic and thermoacoustic tomography," Springer Handb. Math. Methods Imag. (ed. O. Scherzer), pp. 819-865, 2011.

\* cited by examiner

BACKPROJECTION APPROACH FOR PHOTOACOUSTIC IMAGE RECONSTRUCTION

CROSS REFERENCE TO RELATED APPLICATIONS

This application claims priority to, and the benefit of, U.S. provisional application entitled "A PRECISE TIME-DOMAIN BACKPROJECTION APPROACH FOR PHOTOACOUSTIC IMAGE RECONSTRUCTION" having Ser. No. 61/918,365, filed Dec. 19, 2013, which is hereby incorporated by reference in its entirety.

BACKGROUND

Optical imaging techniques have been widely used in a number of important biomedical applications, but they face a serious challenge for deep tissue imaging due to the difficulty of recovery of scattered photons in turbid media. Photoacoustic tomography (PAT), which is based on a hybrid technology that combines rich optical contrast mechanisms and superior ultrasonic penetration depth and resolution, has been demonstrated to successfully address the challenge in conventional optical imaging. Although some basic ideas used for image reconstruction in conventional imaging modalities, such as in computed tomography (CT), may be taken for PAT, significant effort is necessary for adopting those image reconstruction approaches to achieve optimized PAT images due to its unique data acquisition.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
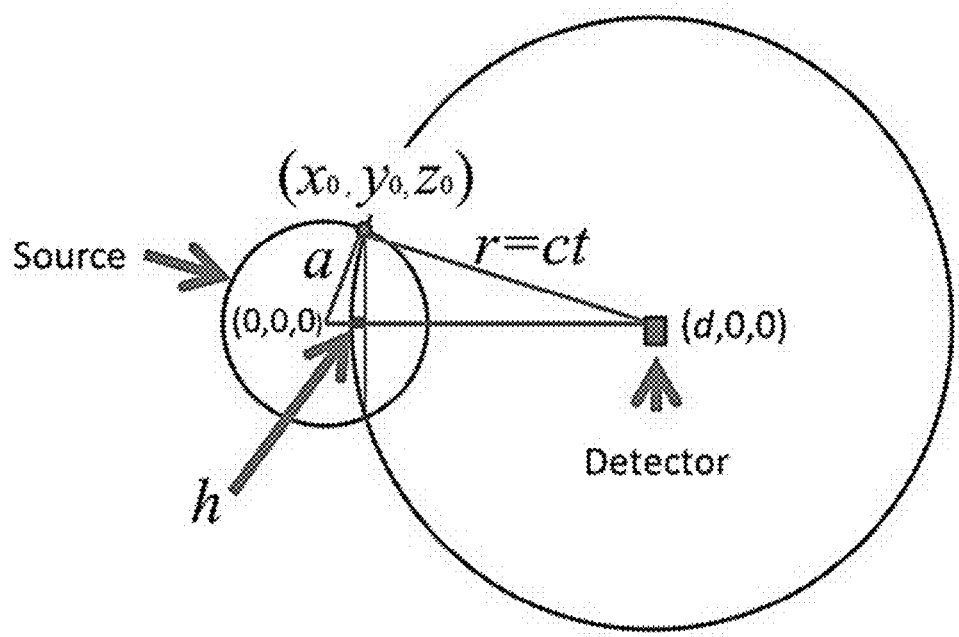
FIG. 1 is a graphical representation illustrating an example of the geometry for detecting photoacoustic signals in accordance with various embodiments of the present disclosure.

Disclosed herein are various examples related to photoacoustic image reconstruction and processing. Various systems and methods that utilize a precise time-domain backprojection approach for photoacoustic image reconstruction and processing are disclosed. Reference will now be made in detail to the description of the embodiments as illustrated in the drawings, wherein like reference numbers indicate like parts throughout the several views.

During photoacoustic tomography (PAT), photons from a short laser pulse are absorbed by certain tissues, causing impulsive heating and acoustic stress in the tissue. The tissue then re-emits the absorbed energy as broadband ultrasonic pressure waves, which propagate to the outside of the tissue where they are detected by a mechanically scanned ultrasound receiver or an array of receivers (or detectors). In the process of photoacoustic imaging formation, the kernel is the algorithm of imaging reconstruction (AIR).

For straightforward back-projection (BP) methods, the reconstructed image is typically blurred. To eliminate the blurring, a variety of methods for BP can be used, such as introducing a negative wing around the raw data in Fourier space before BP. Filtered BP algorithms, which rely on a Space-Space transform, such as Radon transform or Fourier transform, involve filtering before or after BP to provide good reconstructed images for spherical, cylindrical, and planar geometries in simulations.

The arithmetic operator of backprojection is not an inverse operator of projection. Direct backprojection, by converting the projection data at various views into an image, may represent the original object to certain degrees, but it has serious blurring effects. The blurring can be easily understood in the Fourier domain, because Fourier transform can help one understand some hidden mathematical relationships that are not easy to see in the time domain. For example, when a blurred image is analyzed using Discrete Fourier Transform, one can see that higher density of points covers central region of the Fourier space, which is at the low frequency area. This is the root of blurring the image restructured. To overcome the blurring effect, people have put great effort on compensating for the non-uniformity in the Fourier space. Filtered Backprojection (FBP) is most popular image reconstruction algorithm of backprojection that is used in PAT.

Although the filtered BP technique can be useful when solving time dependent partial differential equations using Fourier spectral methods, the image quality can be further improved. For example, the kernel for the BP algorithm used in PAT (e.g., the choice of the negative wing around the raw data in the frequency domain) has been based on only empirical expressions, such as a Cosine window and Hanning window. Despite compelling numerical evidence, there is no general expression to show to what extent the restrictions are on spectrum leakage and picket fence effects by using window functions in Fourier domain for different sampling frequency. In addition, there is no exact criterion about the cutoff frequency of the low pass filter for the negative wing in the frequency domain. In this disclosure, a precise weighting function is disclosed for image reconstruction for PAT. An adaptive criterion has been derived for selecting a low pass filter in the Fourier domain to gain a more precise determination of the cutoff frequency. Numerical simulation results for different phantoms demonstrate the effectiveness of this image reconstruction method for PAT.

During a scan, a plurality of light beams are produced by a source and the produced acoustic signals are detected with one or more detectors. For PAT, acoustic stresses are created inside a tissue after it absorbs energy from a nanosecond laser pulse. The acoustic stresses relax by launching ultrasound waves (i.e., photoacoustic emission), which act as instantaneous acoustic sources. The detection of the ultrasound waves that propagate to the outside of the tissue can be used to reconstruct three dimensional (3D) images of the tissue. The basic physics background and mathematical formula for the photoacoustic waves generation and propagation are described below.

Photoacoustic Wave Equations.

When a short laser pulse irradiates a sample with certain absorbers, the incident light is absorbed (the absorbed energy is H) before the sample density ($\rho$) gets changed. For the case where the laser pulse duration is much shorter than the thermal diffusion time, the thermal diffusion can be neglected, and the thermal equation can be given by:

$$\rho C_p \frac{\partial}{\partial t} T(r,\, t) = H(r,\, t), \tag{1}$$

where $C_p$ is the constant pressure specific heat capacity and T is temperature.

From Newton's Law, the relationship between the pressure distribution function p(r, t) and the acoustic displacement u(r, t) is given by:

$$-\nabla^2 p(r,\, t) - \rho \frac{\partial^2 \nabla \cdot u(r,\, t)}{\partial t^2} = 0. \tag{2}$$

Based on the generalized Hooke's law, the tangential force change is given by:

$$\nabla \cdot u(r,\, t) = -\frac{1}{\rho c^2} p(r,\, t) + \rho(C_p \cdot T(r,\, t)), \tag{3}$$

where c is the wave speed. Putting equation (3) into equation (2) gives:

$$\nabla^2 p(r,\, t) + \rho \frac{\partial^2}{\partial t^2}\left(-\frac{1}{\rho c^2} p(r,\, t) + \rho C_p T(r,\, t)\right) = 0. \tag{4}$$

Therefore, the photoacoustic wave equation can be expressed as:

$$\left(\nabla^2 - \frac{1}{c^2}\frac{\partial^2}{\partial t^2}\right) p(r,\, t) = -\frac{\alpha}{C_p}\frac{\partial H(r,\, t)}{\partial t}. \tag{5}$$

Heating Function.

In most experimental conditions, it is applicable to consider the incident laser pulse having a Gaussian profile with the absorbed energy given by:

$$H(r,\, t) = H(r) \cdot \frac{\exp(t^2/2\tau^2)}{\tau}, \tag{6}$$

where $\tau$ is a characteristic time. From the definition of $$\delta(x) = \lim_{n \to \infty} \sqrt{\frac{n}{\pi}}\, e^{-nx^2},$$

if $c\cdot\tau$ is much shorter than the scale across the "heating" part, or the laser pulse is short enough so that the density of the sample has no time to change, the heating function can be modeled as a Dirac delta function, given by:

$$H(r,t) = H(r)\delta(t). \tag{7}$$

For the photoacoustic effect, this is satisfied when the duration of the laser pulse is much shorter than the time it takes sound to travel across the heated region, a condition known as stress confinement. Under this condition, the photoacoustic wave equation can be written as:

$$\left(\nabla^2 - \frac{1}{c^2}\frac{\partial^2}{\partial t^2}\right) p = -\frac{\alpha}{C_p} H(r)\frac{\partial \delta(t)}{\partial t}. \tag{8}$$

Weighting Function in Fourier Space.

The photoacoustic wave equation (8) has a general solution that can be expressed as:

$$p(r,\, t) = \frac{\alpha}{C_p} \int_{t'=0}^{t'=\infty} \int_V G(r,\, r',\, t,\, t') H(r')\delta'(t')\, d^3r'\, dt', \tag{9}$$

where Green's function is given by $$G(r,\, r',\, t,\, t') = \frac{\delta(|r - r'| - c(t - t'))}{4\pi|r - r'|}.$$

In order to further derive the solution for the photoacoustic wave equation, the following mathematical substitutions are first utilized:

$$\int \delta'(t - t_0) f(t)\, dt = -f'(t_0) \text{ and } \frac{\partial G}{\partial t'} = -\frac{\partial G}{\partial t}.$$

Equation (9) can then be rewritten as:

$$p(r, t) = \frac{\alpha}{C_p} \int_V H(r') \frac{\partial G(r, r', t)}{\partial t} d^3 r'. \quad (10)$$

From the inverse Fourier transform of Green's function, the following can be obtained:

$$G(r, r', t, t') = \frac{1}{(2\pi)^4} \int \int \frac{e^{-ik \cdot (r-r')} e^{j\omega(t-t')}}{k^2 - (\omega/c)^2} d\omega d^3 k. \quad (11)$$

For the frequency axis, it can be seen that there are two simple poles when $\omega = \pm ck$ because:

$$\frac{e^{-ik \cdot (r-r')} e^{j\omega(t-t')}}{k^2 - (\omega/c)^2} = \frac{e^{-ik \cdot (r-r')} e^{j\omega(t-t')}}{(k + \omega/c)(k - \omega/c)}. \quad (12)$$

For t>0, the integration can be calculated based on Cauchy's residue theorem:

$$G(r, r', t) = \frac{c}{(2\pi)^3} \int \frac{\sin(ckt)}{k} e^{ik \cdot (r-r')} d^3 k, \quad (13)$$

which results in:

$$\frac{\partial G(r, r', t)}{\partial t} = \frac{c^2}{(2\pi)^3} \int \cos(ckt) e^{ik \cdot (r-r')} d^3 k. \quad (14)$$

The pressure distribution function p(r, t) can be further derived by utilizing the above equation, giving:

$$p(r, t) = \frac{1}{(2\pi)^3} \int p_0(k) \cos(ckt) e^{ik \cdot r} d^3 k. \quad (15)$$

Since it is known that:

$$p(r, t) = \frac{1}{(2\pi)^3} \int p(k, t) e^{-ik \cdot r} d^3 k. \quad (16)$$

A comparison of equations (15) and (16) shows that, in the Fourier space:

$$p_0(k) = \frac{p(k, t)}{\cos(ckt)} e^{-2ik \cdot r}. \quad (17)$$

Therefore, the initial pressure source function in time domain can be expressed as:

$$p_0(r) = \frac{1}{(2\pi)^3} \int_k p(k, t) W(k, r, t) e^{-ik \cdot r} d^3 k, \quad (18)$$

where $W(k, r, t) = \frac{e^{-2ik \cdot r}}{\cos(ckt)}$ is the weighting function, which represents the amount of contributions from a signal p(k, t) for the image reconstruction in the Fourier domain. Compared with other filtered backprojection methods, this weighting function allows a clear PAT image to be constructed without using an artificial filter, i.e., without using empirically selected window functions in Fourier space. This weighting function has a rigorous form directly derived from the photoacoustic wave equation. As demonstrated in the numerical simulations discussed below, the weighting function plays an important role in determining the image quality in the photoacoustic image reconstruction process.

There are series of singular points when $ckt=\pm\pi/2$. Therefore, in the Fourier domain for a sampling period (T), the cutoff frequency ($f_{cutoff}$) should be chosen using $ckt=\pm\pi/2$ or $2\pi f_{cutoff} T<\pi/2$ to avoid singular points. This allows an objective criterion for setting the cutoff frequency for the disclosed backprojection algorithm. Where $f_{sampling}$ is the sampling rate, then $f_{cutoff}<(f_{sampling}/4)$.

Conventional FBP algorithms require multiplying Fourier transform of projection data by a product of an absolute linear variable, such as $|\omega|$, using window functions for filtering the projection data, and then backprojecting data which are treated in time domain. Ramp-filtering can be implemented as multiplication in the frequency domain or as convolution in the spatial domain. In a weighted FBP algorithm, a weighting function is used in Fourier space, as described in equation (18). The weighted FBP algorithm can be implemented in the following steps: (1) In the frequency domain (k-space), find the Fourier transform of each time-dependent signal p(r) with respect to the variable k, and then obtain the measurement signal p(k) in Fourier space; (2) Multiply p(k) with a ramp filter $\{|\omega t|W\}$ and obtain a new distribution $p_{new}(k)$ in Fourier space, where the cutoff frequency is controlled by the disclosed weighting function W(k, r, t) and sampling rate. $|\omega t|$ is used to correct for a signal with cumulative superposition in Fourier space; (3) Find the inverse Fourier transform of $p_{new}(k)$ with respect to the variable k, and then obtain the projection signal $p_{new}(r, t)$; and (4) Accumulate the signals from $p_{new}(r, t)$ for each backprojection position, transfer the accumulated signal value to the grey scale value, and then obtain the reconstructed image.

Most ramp filters for an image reconstruction algorithm is a high-pass filter (e.g., the ramp filter $|\omega|$) in which the high-frequency components are enhanced more than the low-frequency components. Also, in order to suppress the high-frequency noise, an empirical window function, such as a Hanning window, is typically applied to the ramp filter in conventional FBP. In contrast, in step (2) of the weighted FBP algorithm, a time-dependent dimensionless quantity $|\omega t|$ combined with a unique weighting function as in equation (18) is used as the ramp filter. In addition, the weighted FBP algorithm provides a decisive way for determining an adaptive cutoff frequency based on the sampling rate.

The weighted FBP algorithm can be utilized for image reconstruction and image processing, which is not just restricted to the acoustic detection. The weighted FBP algorithm has wide applications in a number of important fields including medical imaging, strata configuration, underwater target, astrophysics detection, photography, etc.

The existing image reconstruction technology cannot produce image quality as good as that generated with the weighted FBP algorithm. In addition, it can be used to detect the ringing effect area of an image with significantly higher accuracy compared to commercial methods including Canny edge detection.

In order to test the weighted FBP algorithm, numerical simulations were conducted on different phantom samples, which comprise several spherical absorbers arranged in different configurations and suspended in a non-absorbing medium. Consider a planar measurement configuration, where one or more acoustic detector is scanned on a plane to receive the photoacoustic emission signals from the absorbers.

For the numerical simulation, a data set of the photoacoustic signals from a phantom sample can be used. To establish a method for building the data set, first consider a general situation, where the photoacoustic signals emitted from a spherical absorber located at position (0, 0, 0) are detected with a point detector at (d, 0, 0). FIG. 1 illustrates an example of the geometry of detecting photoacoustic signals from a single absorber by a point detector. The signal received at time t can be from anywhere on the surface of a sphere with a radius r=ct and having its center at the position of the detector. The coordinates $(x_0, y_0, z_0)$ describe a circle of the interface between the absorber surface and the detection surface. In addition, h denotes the height of the hat, while a is the radius of the absorber sphere.

For measurements with a certain sampling frequency, the detected signal at a distance r=ct comes from a volume element $\Delta$Volumn=Area·(c$\Delta$t), where $\Delta$t is the time duration of the measurement that depends on the sampling frequency, and Area=$2\pi h \cdot r = 2\pi h \cdot ct$. If the absorber has a uniform photoacoustic emission when irradiated with a laser pulse, and the signal intensity per unit volume has a value A, then the measured signal at time t can be described as:

$$|p(t)| = \frac{A \cdot \Delta \text{Volumn}}{ct} = A \cdot 2\pi c \Delta t \frac{a^2 - (ct-d)^2}{d}. \quad (19)$$

In practice, a detector has certain dimension rather than an ideal point detector. In the numerical simulation, a detector was divided into a number of small elements to approximate the actual detector. The total signal received by the detector can then be computed by a summation as:

$$|p(d,t)| = \begin{cases} \sum_i A \frac{a^2 - (ct-d_i)^2}{d_i}, & a - |d_i - ct| > 0 \\ 0, & a - |d_i - ct| < 0. \end{cases} \quad (20)$$

where $d_i$ is the position of the ith detector element.

In the following simulations, it is assumed that a rectangular-shaped detector moves in a plane along both x and y axes from −30.0 mm to 30.0 mm with a spatial sampling period of ⅔ mm. Therefore, the photoacoustic signals are collected at 8,281 (91×91) total positions. The detector surface was divided into 25 elements to obtain more realistic signals. The data sampling frequency was set to be 20.48 MHz. Based on the discussion above, the cutoff frequency for a low pass filter is set to 5.0 MHz to generate negative wing for projection of data in time domain. The smallest size of the absorber used in the simulation was set to 1.0 mm. In order to test if the weighted FBP algorithm can still generate high quality images even under poor measurement conditions, a low spatial resolution of the reconstructed image was chosen with 91×91 pixels for each cross-sectional reconstructed image in the numerical simulations. The used parameter corresponds to a detected area of 45.0 mm×45.0 mm with a spatial resolution of 0.495 mm per pixel.

Figure 2:
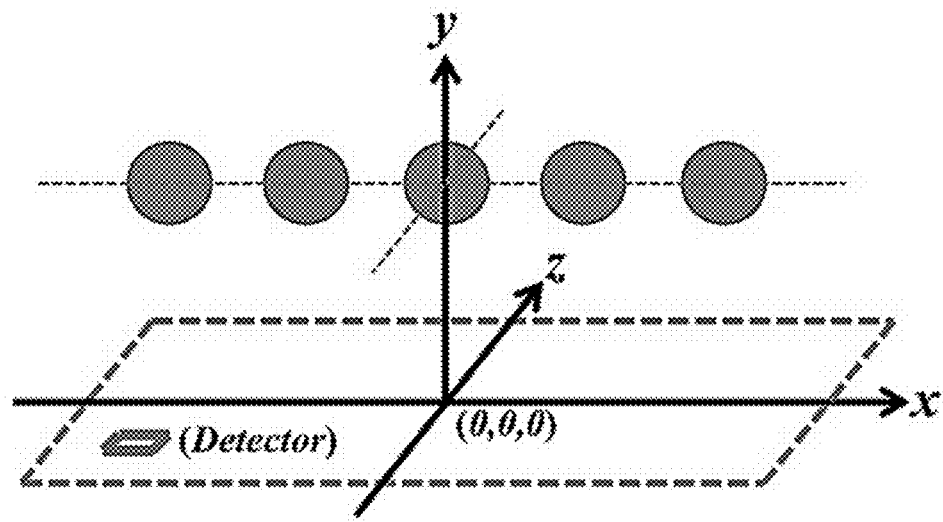
FIGS. 2 and 5 are graphical representations illustrating examples of the geometries of phantom samples or absorbers used for simulations of photoacoustic image reconstruction in accordance with various embodiments of the present disclosure.

A first numerical simulation was designed to test the geometry and the contour of cross sectional images. The phantom sample used contains five uniform spherical absorbers, which are arranged on a plane with a distance of 15.0 mm to the detection plane. FIG. 2 is a graphical representation of the geometry of the phantom sample used for the first simulation. Each spherical absorber had a radius of 1.5 mm. The center position of the absorbers were at (−18.0, 0.0, 15.0), (−9.0, 0.0, 15.0), (0.0, 0.0, 15.0), (9.0, 0.0, 15.0) and (18.0, 0.0, 15.0) in a unit of mm, respectively. The relative intensities per unit volume were 1.0, 2.0, 3.0, 4.0, and 5.0 for the absorbers counted from left to right, respectively.

Figure 3A:
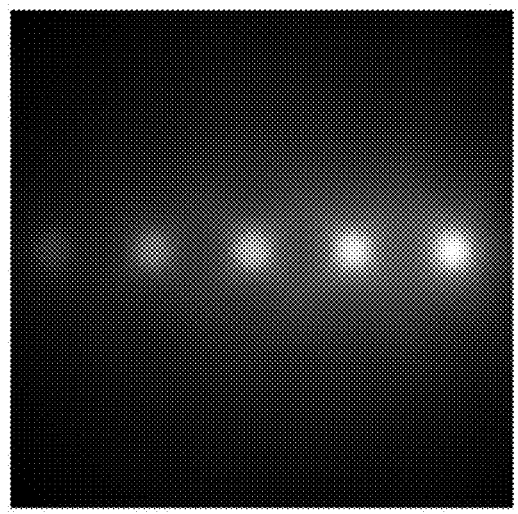
FIGS. 3A and 3B illustrate the results of photoacoustic image reconstruction of the geometry of FIG. 2 using direct backprojection in accordance with various embodiments of the present disclosure.
Figure 3B:
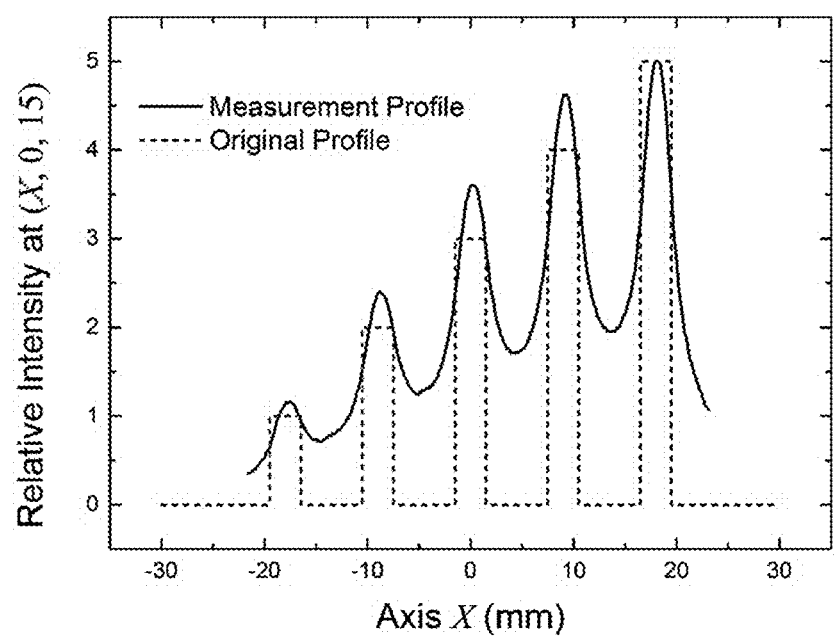

Referring to FIGS. 3A and 3B, shown is an example of the first simulation using a direct backprojection method. A cross section of a reconstructed image from the direct backprojection is shown in FIG. 3A, with the reconstructed image at the plane z=15.0 mm. Although the image shows the basic geometry of the phantom sample, the object is seriously blurred. FIG. 3B shows the relative intensities of the absorbers in the reconstructed image of FIG. 3A at a cross section plane of (X, 0, 15). It can be seen that the intensities of the absorbers deviate from the actual value significantly.

Figure 4A:
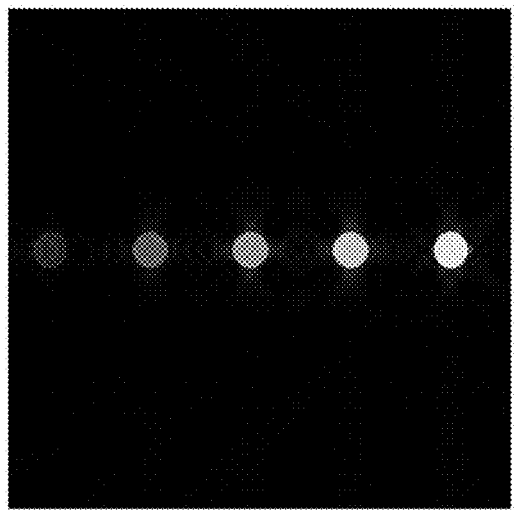
FIGS. 4A and 4B illustrate the results of photoacoustic image reconstruction of the geometry of FIG. 2 using weighted filtered backprojection (FBP) in accordance with various embodiments of the present disclosure.
Figure 4B:
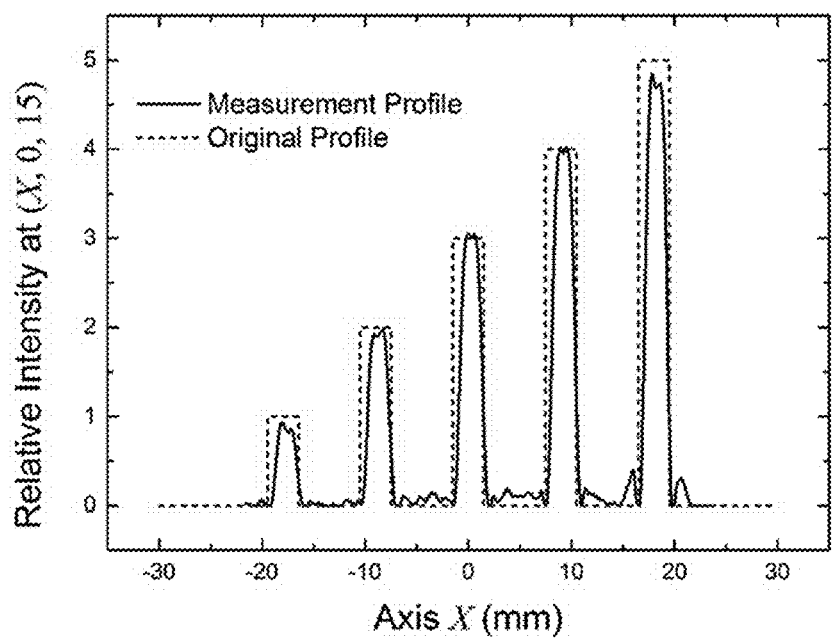

Referring next to FIGS. 4A and 4B, shown is an example of the first simulation using the weighted FBP method. A cross section of a reconstructed image from the weighted FBP is shown in FIG. 4A, with the reconstructed image at the plane z=15.0 mm. In sharp contrast to the DBP results, the quality of the image reconstructed with the weighted FBP algorithm has been significantly improved. This is further illustrated by FIG. 4B, which shows the relative intensities of the absorbers in the reconstructed image of FIG. 4A at a cross section plane of (X, 0, 15).

The weighted FBP algorithm multiplies the Fourier signals with the ramp filter $\{|\omega t|W\}$ defined in equation (18) before backprojection. The treated signals can then be projected back to the time domain. The unique form of the ramp filter and the signal processing allow for a remarkable reduction of the blurring effect. Instead of using an empirical window function, such as a Hanning window as in the conventional FBP, the weighted FBP algorithm utilizes a weighting function W that has a rigorous form directly derived from the photoacoustic wave equation. Furthermore, this approach allows not only a sharp image (FIG. 4A) to be obtained, but also can correct signal strength from the absorbers that matches well with the values of the absorption assumed for each absorber (FIG. 4B).

Figure 5:
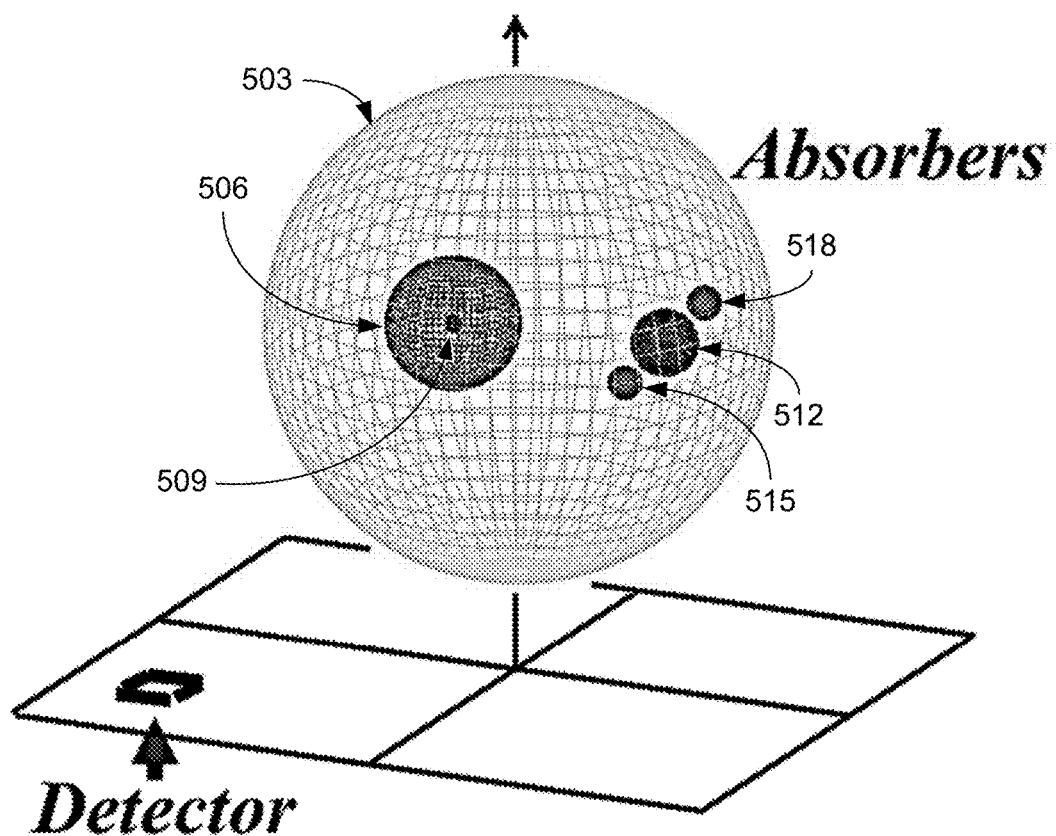

A second numerical simulation was designed to test a phantom sample having absorbers with different sizes and having overlapping areas. FIG. 5 is a graphical representation of the geometry of the absorbers used for the second simulation. Six spherical absorbers 503-518 were arranged in an overlapping arrangement as shown. Their center positions were at (0.0, 0.0, 15.0), (−4.0, 0.0, 15.0), (−4.0, 0.0, 15.0), (9.0, 0.0, 15.0), (9.0, −8.0, 15.0) and (9.0, 8.0, 15.0), respectively, where the coordinate unit is millimeter. The first sphere 503 contained the other five spherical absorbers 506-518, while the second sphere 506 further contained the third sphere 509. The six spherical absorbers 503-518 had a radius of 15.0, 4.0, 0.5, 2.0, 1.0 and 1.0 mm, respectively.

For the first sphere 503 the intensity per unit volume was 1.0 except for the overlapping area. The second sphere 506 had an intensity per unit volume of 2.0 except for the overlapping area. For the third through sixth spheres 509, 512, 515, and 518 the intensity per unit volume was 3.0, 3.0, 2.0, and 2.0, respectively.

Figure 6A:
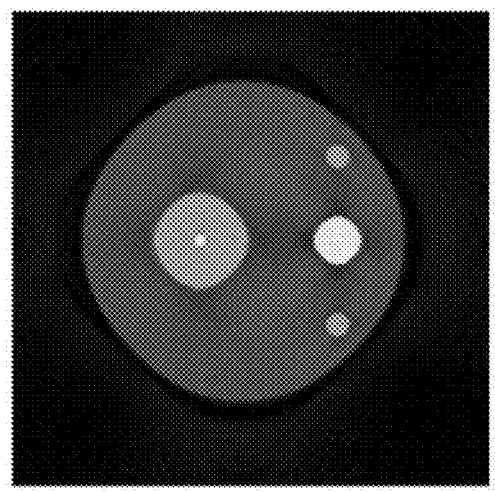
FIGS. 6A-6D and 7A-7D illustrate the results of photoacoustic image reconstruction of the geometry of FIG. 5, without and with noise present, using weighted FBP in accordance with various embodiments of the present disclosure.

The performance of the weighted FBP algorithm was evaluated for this complicated geometry. In addition, a noise source was added to the observed signals to mimic more realistic experimental conditions. The arrangement of the detector was the same as that in the first simulation. The simulation of the phantom sample was first performed without noise, which is illustrated in FIGS. 6A through 6D. FIG. 6A is a gray scale image of the reconstructed cross sectional image using the weighted FBP, in the plane of z=15 mm. The reconstructed image of FIG. 6A is sharp and represents well the geometry of the absorbers 503-518. Although some small artificial structures can be seen around the reconstructed images of the absorbers 503-518, they are minimal and may be attributed to the limited detection angle and bandwidth.

Figure 6B:
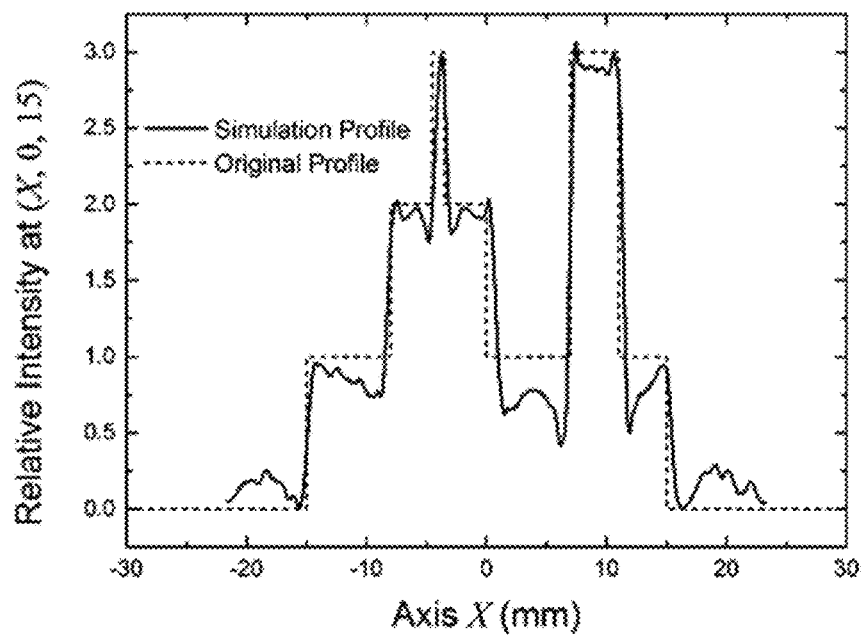
Figure 6C:
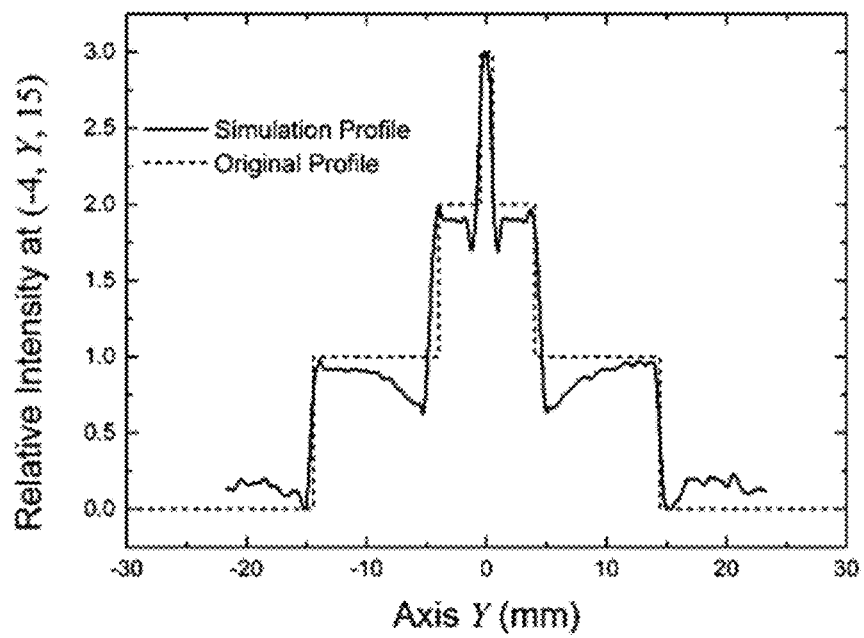
Figure 6D:
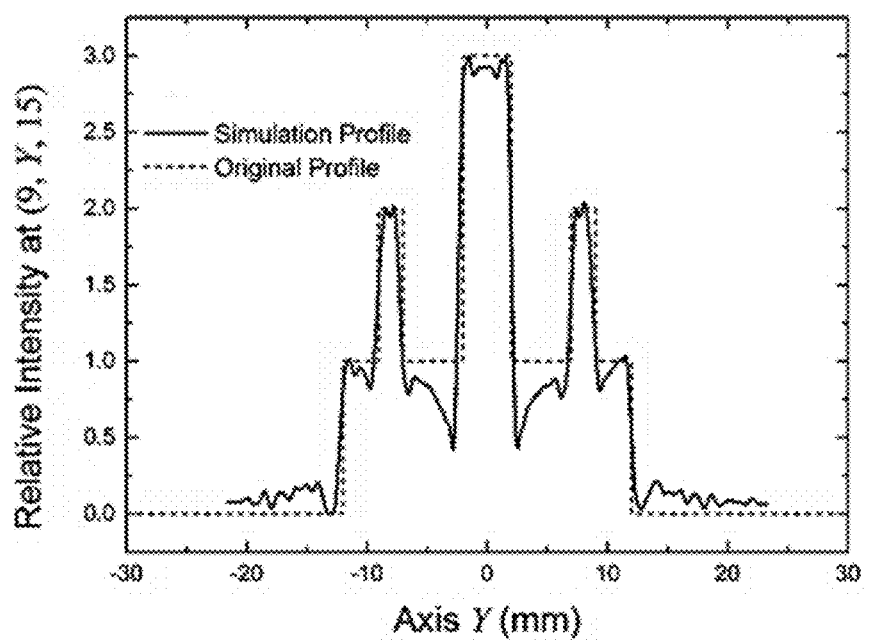

FIGS. 6B, 6C, and 6D C a comparison of the relative intensities between the original and the reconstructed distributions along the lines at (X, 0, 15), (−4, Y, 15) and (9, Y, 15), respectively. The reconstructed intensity profiles are sharp and the values match well with the original ones. The high quality of the reconstructed images demonstrate the advantages of the weighted FBP algorithm, which utilizes the rigorously derived weighting function in the Fourier domain and a precise cutoff frequency rather than using an empirical filter function as in conventional FBP.

Figure 7A:
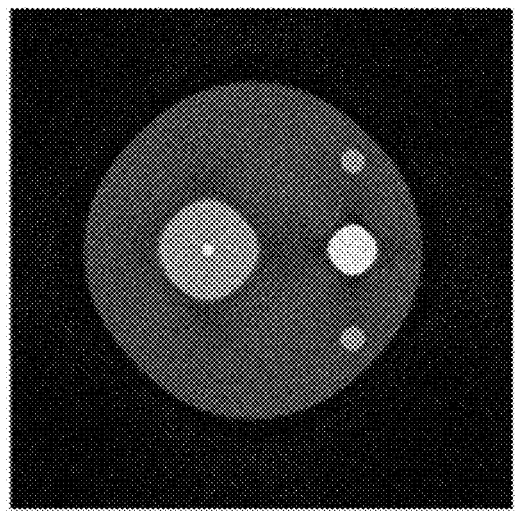

Next, the case with additional noise in the measurements was examined. If the noise term is added into equation (20), then $$|p(d, t)| = \begin{cases} \sum_i A \frac{a^2 - (ct - d_i)^2}{d_i} + \text{noise}, & a - |d_i - ct| > 0 \\ \text{noise}, & a - |d_i - ct| < 0. \end{cases} \quad (21)$$

where the noise signal is a series of computer-generated random numbers with values between −0.1 and 0.1. FIGS. 7A through 7D illustrate the second simulation with noise added to the observed signals. FIG. 7A is a reconstructed gray-scale image of the cross section of the absorbers in the plane of z=15 mm with noise introduced to the observed signals. Although noise appears in the image, FIG. 7A is still clear enough to provide a good presentation of the geometry of the absorbers 503-518.

Figure 7B:
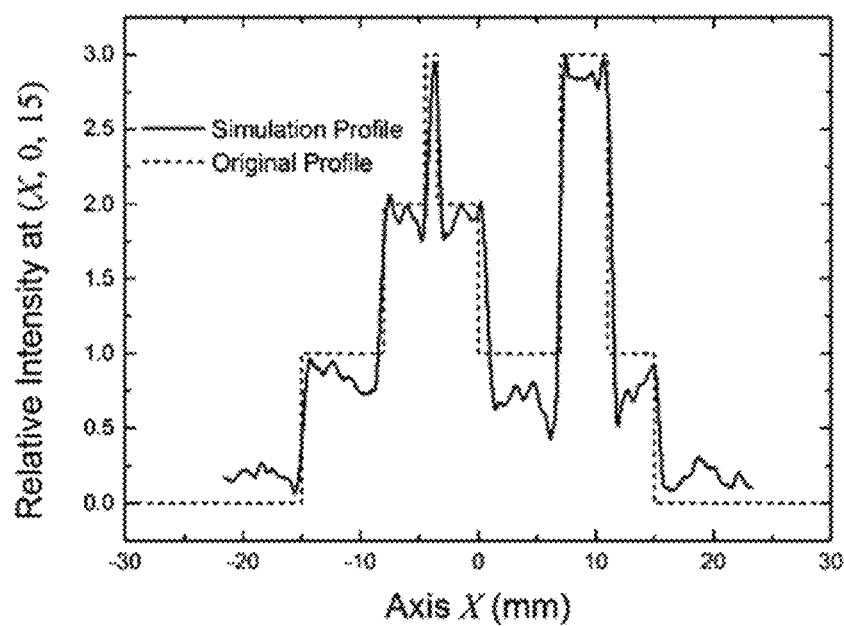
Figure 7C:
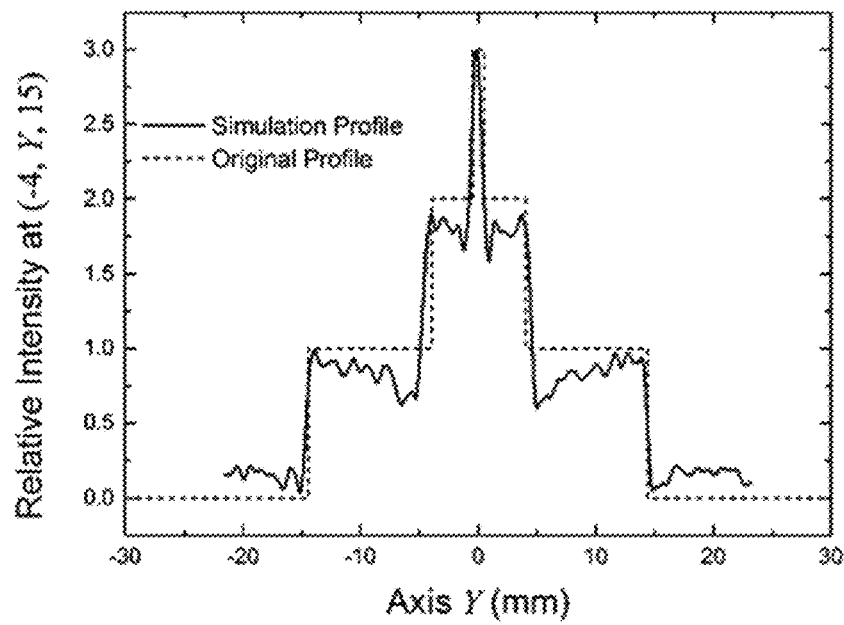
Figure 7D:
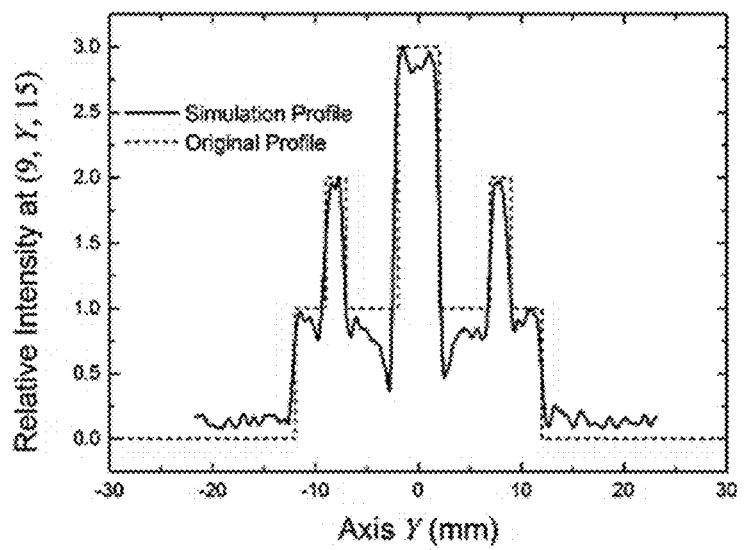

FIGS. 7B, 7C, and 7D are plots that show a comparison of the relative intensities between the original and the reconstructed intensity distributions along the lines (X, 0, 15), (−4, Y, 15) and (9, Y, 15), respectively. Despite certain noise, the reconstructed intensity profiles are still in good agreement with the original ones. The fact that the noise remains at a minimal level demonstrates the robustness of the weighted FBP algorithm for reconstructing PAT images of complicated structures when a reasonable amount of detection noise is present.

It is worth noting that even under the assumed poor detection condition with a spatial resolution of 0.495 mm/pixel, the reconstructed image still produces a good reproduction of the geometry of the smallest absorber, i.e., the third sphere 509 with a radius of 0.5 mm for both of the cases: without detection noise (FIGS. 6A-6D) or with detection noise (FIGS. 7A-7D).

Figure 8:
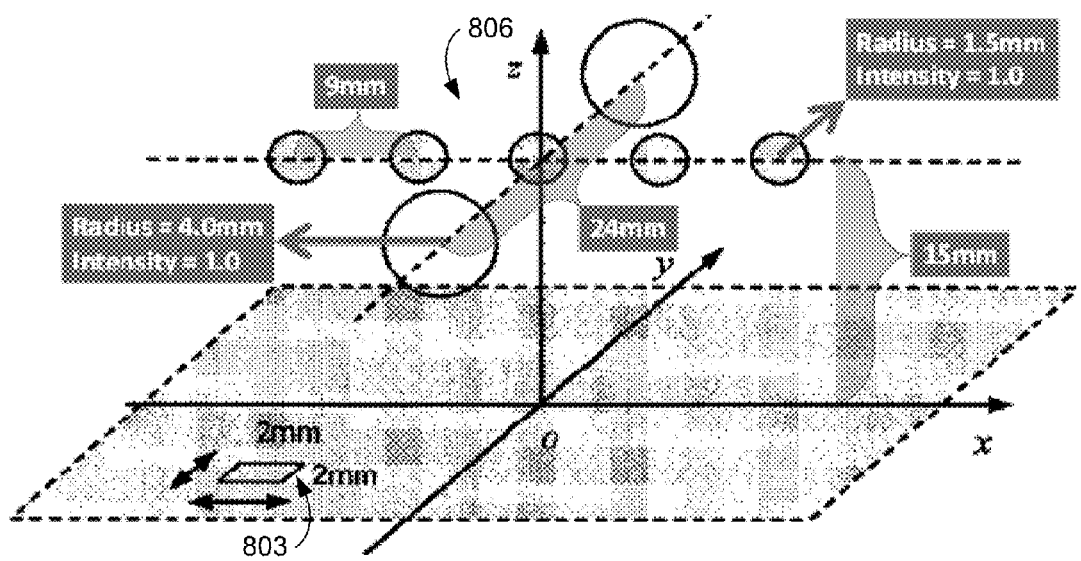
FIG. 8 is an example of a photoacoustic imaging system including a geometry of samples in accordance with various embodiments of the present disclosure.
Figure 9B:
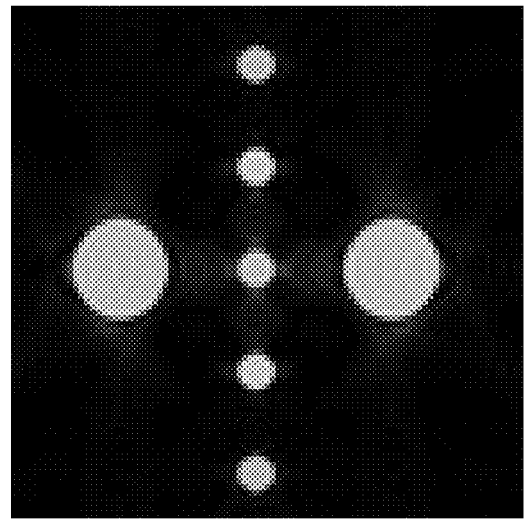
FIGS. 9A and 9B illustrate the results of photoacoustic image reconstruction of the geometry of FIG. 8 without and with the surfaces of the detector divided into elements for processing in accordance with various embodiments of the present disclosure.
Figure 9A:
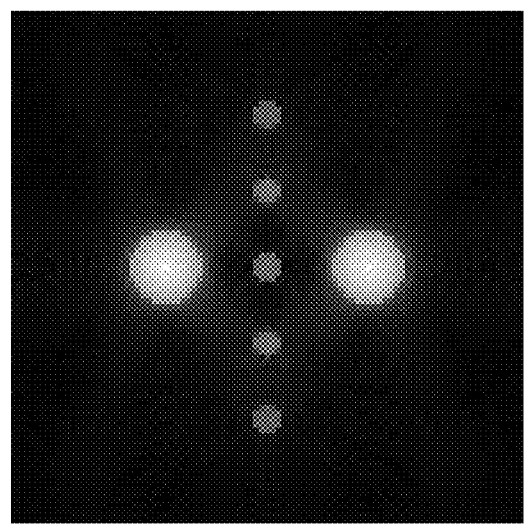

Referring now to FIG. 8, shown is an example of a photoacoustic imaging system 800. The system can include a plurality of acoustic detector units configured to receive an acoustic wave generated by irradiating a subject with light emitted from a light source and to convert the acoustic wave to an electrical signal, and a processing unit configured to reconstruct images of the subject using backprojection. As illustrated in FIG. 8, a rectangular-shaped detector (2 mm×2 mm) 803, scans the samples arranged in the z=0 plane 806 along both the x and y axes from −30 mm to 30 mm with a spatial sampling period of ⅔ mm, where the center of the detector surface represents its position. In the computation of the photoacoustic signal of the detector, the surfaces of the detector 803 were evenly divided into 25 small elements. FIG. 9A shows a reconstructed image using conventional methods and FIG. 9B shows a reconstructed image using the weighted FBP based upon the 25 divided elements of the detector 803 and equation (20). As can be seen, the weighted FBP considering a divided detector provides a clearer reconstructed image than conventional methods.

Figure 10B:
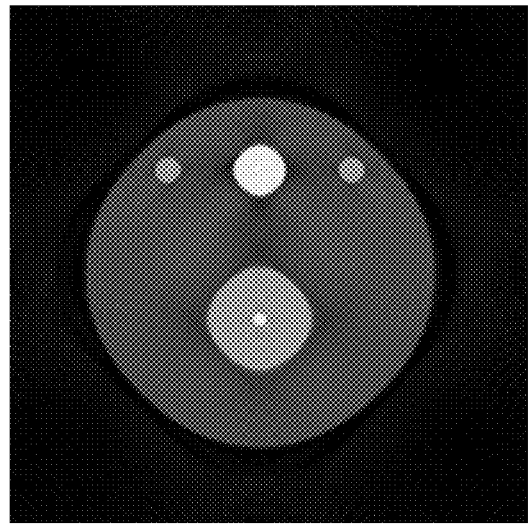
FIGS. 10A and 10B illustrate ringing effects on photoacoustic image reconstruction in accordance with various embodiments of the present disclosure.
Figure 10A:
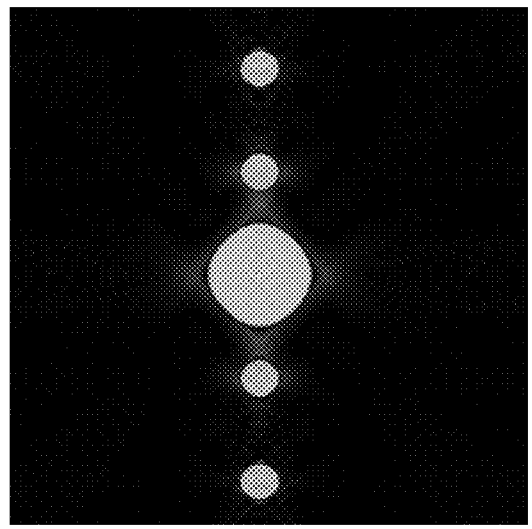

Detection of the ringing effect can also be performed. Ringing effects are the artifacts that appear as spurious signals near sharp transitions in a signal. Referring to FIGS. 10A and 10B, shown are examples of ringing effects. FIG. 10B shows a reconstructed image for the second numerical simulation affected by ringing effect.

Figure 11:
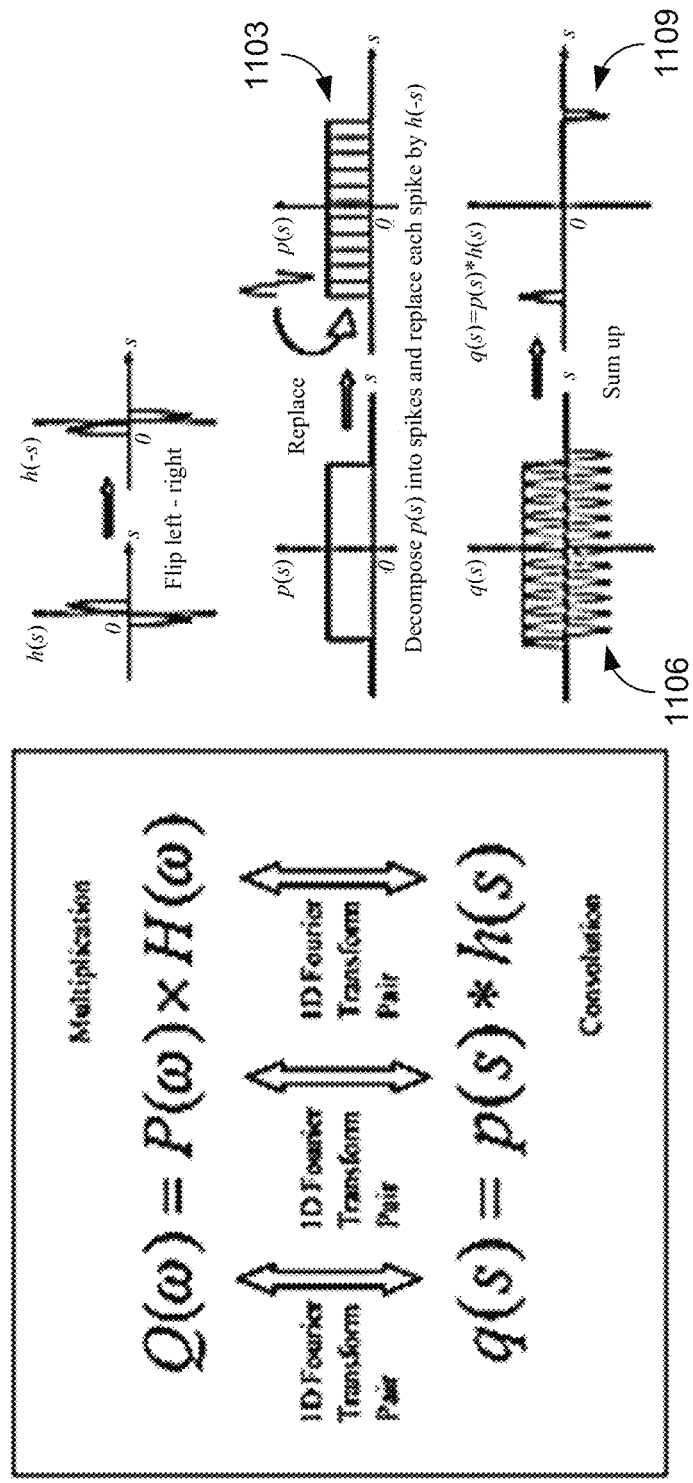
FIG. 11 illustrates an example of the detection of the edge or area of ringing effects in accordance with various embodiments of the present disclosure.

FIG. 11 shows an example of the detection of the edge or area of ringing effects. The illustrated example is based on a convolution method. First, an antisymmetric function is selected as a convolution kernel h(s). Second, the function p(s) that represents the intensity or other physical quantity of an image is decomposed into a series of discrete spikes (or Dirac delta functions) along the axis of s, as illustrated by 1103. Third, each spike is replaced by h(−s) in a way that the center position of h(−s) is set to the spike's position and the value of h(−s) is multiplied by the value of the spike, as illustrated by 1106. Finally, convolution between the function created at 1106 and h(s) is taken to obtain a function q(s), as illustrated by 1106. The function q(s) has non-zero values close to the edge of the function p(s).

Figure 12C:
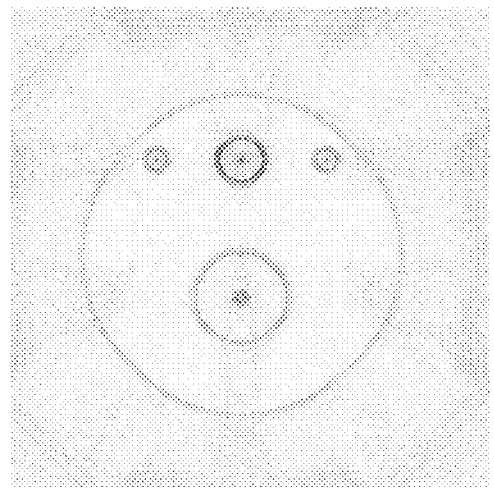
FIGS. 12A-12C and 13A-13B illustrate examples of results from the detection of the edge and area of ringing effects of FIG. 11 in accordance with various embodiments of the present disclosure.
Figure 12B:
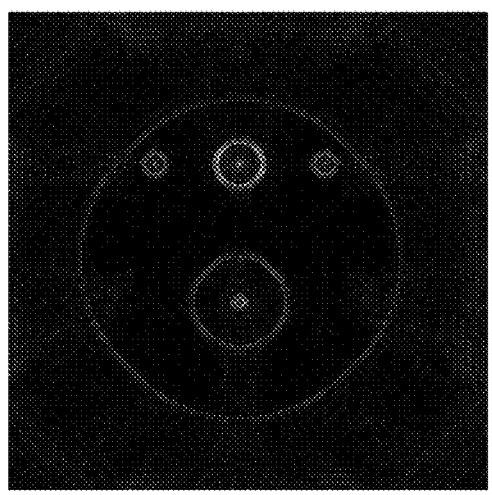
Figure 12A:
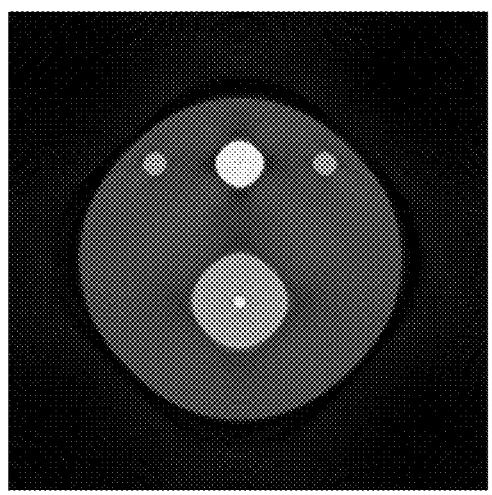
Figure 13B:
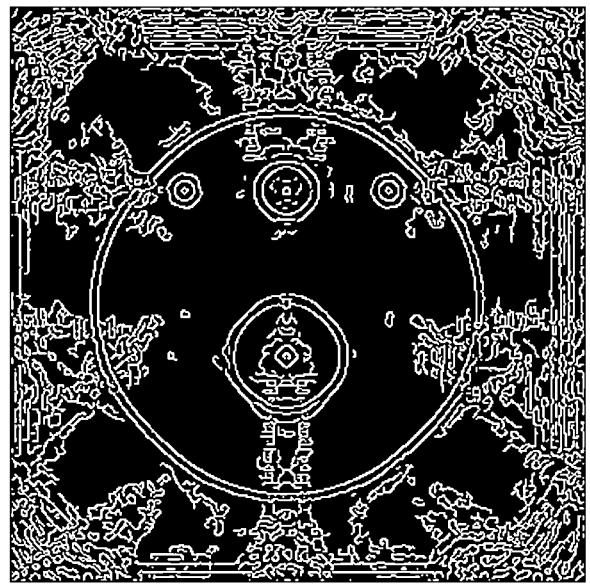
Figure 13A:
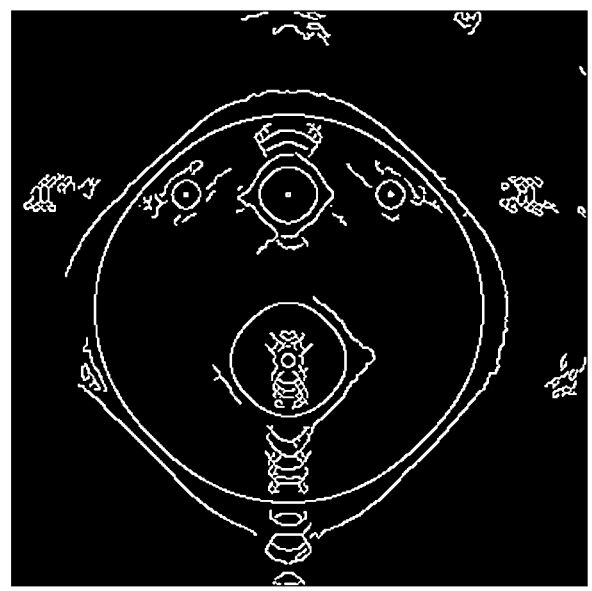

FIGS. 12A-12C and 13A-13B illustrate examples of the results of this detection process. FIG. 12A shows the reconstructed image for the second numerical simulation affected by ringing effect. FIGS. 12B and 12C show the edge detection results using the method of FIG. 11. As can be seen, the edges of the spherical absorbers 503-518 are identified. FIGS. 13A and 13B compares the results of area of the ringing effect using Canny edge detection and convolution edge detection of FIG. 11. FIG. 13A shows the results for the Canny edge detection and FIG. 13B shows the results for the convolution edge detection.

Another embodiment of the present disclosure includes a photoacoustic imaging system comprising a plurality of acoustic detector units configured to receive an acoustic wave generated by irradiating a subject with light emitted from a light source and to convert the acoustic wave to an electrical signal; and a processing unit configured to reconstruct three dimensional (3D) images of the subject using weighted FBP. The processing includes: (1) in the frequency domain (k-space), finding a Fourier transform of each time-dependent signal p(r) with respect to the variable k, and then obtaining the measurement signal p(k) in the Fourier space; (2) multiplying p(k) with a ramp filter {|ωt|W} and obtaining a new distribution $p_{new}(k)$ in the Fourier space, where the cutoff frequency is controlled by the disclosed weighting function W(k, r, t) and sampling rate (|ωt| is used to correct for a signal with cumulative superposition in the Fourier space); (3) finding the inverse Fourier transform of $p_{new}$(k) with respect to the variable k, and then obtaining the projection signal $p_{new}$(r, t); and (4) accumulating the signals from $p_{new}$(r, t) for each backprojection position, transferring the accumulated signal value to the grey scale value, and then obtaining the reconstructed image.

The signal processing unit can be composed of, for example, a computer that is provided with a CPU (central processing unit), a main storage (memory), an auxiliary storage (hard disk, etc.), an input device, and/or so on. A program or application for achieving the function of the signal processing unit can be stored in the auxiliary storage of the computer for implementation by the CPU. The CPU can load the program into the main storage from the auxiliary storage and execute it, so that processing comprising the steps of: (1) In the frequency domain (k-space), find the Fourier transform of each time-dependent signal p(r) with respect to the variable k, and then obtain the measurement signal p(k) in the Fourier space; (2) Multiply p(k) with a ramp filter {|ωt|W} and obtain a new distribution $p_{new}$(k) in the Fourier space, where the cutoff frequency is controlled by the disclosed weighting function and sampling rate (|ωt| is used to correct for a signal with cumulative superposition in the Fourier space); (3) Find the inverse Fourier transform of $p_{new}$(k) with respect to the variable k, and then obtain the projection signal $p_{new}$(r, t); and (4) Accumulate the signals from $p_{new}$(r, t) for each backprojection position, transfer the accumulated signal value to the grey scale value, and then obtain the reconstructed image; are executed, and data analysis of the measurement data is carried out. A display device can be used to display image data created by the signal processing unit. For example, a liquid crystal display or the like can be used.

In another embodiment, a non-transitory computer readable medium stores a program or application for causing a computer to perform the steps of: (1) in the frequency domain (k-space), finding a Fourier transform of each time-dependent signal p(r) with respect to the variable k, and then obtaining the measurement signal p(k) in the Fourier space; (2) multiplying p(k) with a ramp filter {|ωt|W} and obtaining a new distribution $p_{new}$(k) in the Fourier space, where the cutoff frequency is controlled by the disclosed weighting function W(k, r, t) and sampling rate (|ωt| is used to correct for a signal with cumulative superposition in the Fourier space); (3) finding the inverse Fourier transform of $p_{new}$(k) with respect to the variable k, and then obtaining the projection signal $p_{new}$(r, t); and (4) accumulating the signals from $p_{new}$(r, t) for each backprojection position, transferring the accumulated signal value to the grey scale value, and then obtaining the reconstructed image.

A computer of a system or apparatus (or devices such as a CPU or MPU or GPU) that reads out and executes a program recorded on a memory device can be utilized to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., non-transitory computer-readable medium).

Figure 14:
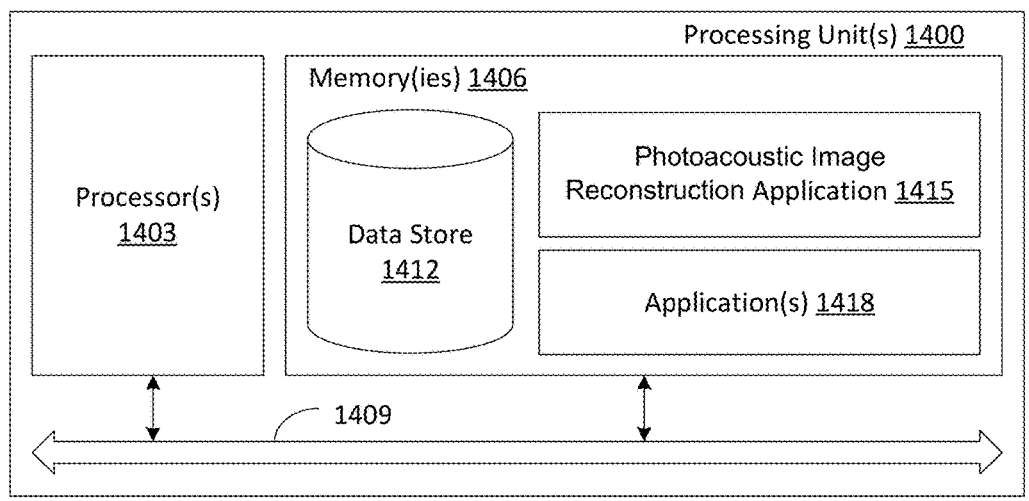
FIG. 14 is a schematic block diagram of a processing unit in accordance with various embodiments of the present disclosure.

With reference to FIG. 14, shown is a schematic block diagram of a processing unit 1400 according to various embodiments of the present disclosure. The processing unit 1400 includes at least one processor circuit, for example, having a processor 1403 and a memory 1406, both of which are coupled to a local interface 1409. To this end, the processing unit 1400 may comprise, for example, at least one server computer or like device. The local interface 1409 may comprise, for example, a data bus with an accompanying address/control bus or other bus structure as can be appreciated.

Stored in the memory 1406 are both data and several components that are executable by the processor 1403. In particular, stored in the memory 1406 and executable by the processor 1403 may be a photoacoustic image reconstruction application 1415 and/or other applications 1418. Also stored in the memory 1406 may be a data store 1412 and other data. In addition, an operating system may be stored in the memory 1406 and executable by the processor 1403.

It is understood that there may be other applications that are stored in the memory 1406 and are executable by the processor 1403 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Delphi®, Flash®, or other programming languages.

A number of software components are stored in the memory 1406 and are executable by the processor 1403. In this respect, the term "executable" means a program file that is in a form that can ultimately be run by the processor 1403. Examples of executable programs may be, for example, a compiled program that can be translated into machine code in a format that can be loaded into a random access portion of the memory 1406 and run by the processor 1403, source code that may be expressed in proper format such as object code that is capable of being loaded into a random access portion of the memory 1406 and executed by the processor 1403, or source code that may be interpreted by another executable program to generate instructions in a random access portion of the memory 1406 to be executed by the processor 1403, etc. An executable program may be stored in any portion or component of the memory 1406 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 1406 is defined herein as including both volatile and nonvolatile memory and data storage components. Volatile components are those that do not retain data values upon loss of power. Nonvolatile components are those that retain data upon a loss of power. Thus, the memory 1406 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 1403 may represent multiple processors 1403 and the memory 1406 may represent multiple memories 1406 that operate in parallel processing circuits, respectively. In such a case, the local interface 1409 may be an appropriate network that facilitates communication between any two of the multiple processors 1403, between any processor 1403 and any of the memories 1406, or between any two of the memories 1406, etc. The local interface 1409 may comprise additional systems designed to coordinate this communication, including, for example, performing load balancing. The processor 1403 may be of electrical or of some other available construction.

Although the photoacoustic image reconstruction application 1415, application(s) 1418, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Although FIG. 1 shows a specific order of execution, it is understood that the order of execution may differ from that which is depicted. For example, the order of execution of two or more blocks may be scrambled relative to the order shown. Also, two or more blocks shown in succession in FIG. 1 may be executed concurrently or with partial concurrence. Further, in some embodiments, one or more of the blocks shown in FIG. 1 may be skipped or omitted (in favor, e.g., measured travel times). In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the photoacoustic image reconstruction application 1415 and/or application(s) 1418, that comprises software or code can be embodied in any non-transitory computer-readable medium for use by or in connection with an instruction execution system such as, for example, a processor 1403 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

With this disclosure, examples of methods and systems have been presented for image reconstruction in photoacoustic tomography utilizing a weighted FBP algorithm. In contrast to conventional backprojection techniques that generally utilize different empirical window functions, an exact form of a weighting function has been derived from the basic photoacoustic wave equation. The weighting function serves as a precise ramp filter for processing the observed signals in the Fourier domain. In contrast to relying on empirically selected window functions as filters, the weighted FBP utilizes the mathematically determined weighting function to precisely count the contribution from a photoacoustic signal for the image reconstruction in Fourier domain. In addition, the weighted FBP algorithm allows for a precise determination of the cutoff frequency based on the chosen weighting function and sampling rate. An adaptive criterion has been derived for selecting a cutoff frequency in Fourier domain based on the weighting function and the used sampling rate. The treated data are then converted back to the time domain through inverse Fourier transform and are then used for backprojection.

A series of numerical simulations on different phantom samples have been conducted. The results have demonstrated the effectiveness of using this method for image reconstruction in photoacoustic tomography with significantly improved image quality. High-quality reconstructed images can be produced even for complicated sample structures and/or in the presence of noise in the observed signals. The disclosed system and method of use was generally described, with examples incorporated as particular embodiments of the disclosure and to demonstrate the practice and advantages thereof. It is understood that the examples are given by way of illustration and are not intended to limit the specification or the claims in any manner.

To facilitate the understanding of this disclosure, a number of terms may be defined below. Terms defined herein have meanings as commonly understood by a person of ordinary skill in the areas relevant to the present disclosure. Terms such as "a", "an", and "the" are not intended to refer to only a singular entity, but include the general class of which a specific example may be used for illustration. The terminology herein is used to describe specific embodiments of the disclosure, but their usage does not delimit the disclosed device or method, except as may be outlined in the claims. In the claims, all transitional phrases such as "comprising," "including," "carrying," "having," "containing," "involving," and the like are to be understood to be open-ended, i.e., to mean including but not limited to. Only the transitional phrases "consisting of" and "consisting essentially of," respectively, shall be closed or semi-closed transitional phrases.

Alternative applications of the disclosed system and method of use are directed to image reconstruction. Consequently, any embodiments comprising a one component or a multi-component system having the structures as herein disclosed with similar function shall fall into the coverage of claims of the present disclosure and shall lack the novelty and inventive step criteria. It will be understood that particular embodiments described herein are shown by way of illustration and not as limitations of the disclosure. The principal features of this disclosure can be employed in various embodiments without departing from the scope of the disclosure. Those skilled in the art will recognize, or be able to ascertain using no more than routine experimentation, numerous equivalents to the specific device and method of use described herein. Such equivalents are considered to be within the scope of this disclosure and are covered by the claims.

The systems and/or methods disclosed and claimed herein can be made and executed without undue experimentation in light of the present disclosure. While the system and methods of this disclosure have been described in terms of preferred embodiments, it will be apparent to those skilled in the art that variations may be applied to the system and/or methods and in the steps or in the sequence of steps of the method described herein without departing from the concept, spirit, and scope of the disclosure. More specifically, it will be apparent that certain components, which are both shape and material related, may be substituted for the components described herein while the same or similar results would be achieved. All such similar substitutes and modifications apparent to those skilled in the art are deemed to be within the spirit, scope, and concept of the disclosure as defined by the appended claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A method for producing an image with a photoacoustic imaging system, comprising:
   scanning an object with a plurality of light beams produced by a source;
   detecting, with a detector, a plurality of acoustic signals propagating through the object, the plurality of acoustic signals produced by absorption of the plurality of light beams by the object; and
   generating, with processing circuitry, a reconstructed image of the object from the plurality of acoustic signals by filtered backprojection (FBP), where the FBP utilizes a weighted ramp filter applied in Fourier space, where the weighted ramp filter varies over the Fourier space and is defined as $\{|\omega t|W\}$, where $$W(k, r, t) = \frac{e^{-2ik \cdot r}}{\cos(ckt)}$$

is a weighting function.

2. The method of claim 1, wherein generating the reconstructed image by FBP comprises:
   determining a plurality of measurement signals p(k) in a frequency domain k-space; and
   multiplying the plurality of measurement signals p(k) with the weighted ramp filter to obtain a plurality of weighted measurement signals $p_{new}(k)$.

3. The method of claim 2, wherein generating the reconstructed image by FBP further comprises:
   obtaining a plurality of projection signals $p_{new}(r, t)$ by inverse Fourier transform of the plurality of weighted measurement signals $p_{new}(k)$ with respect to k of the k-space; and
   accumulating the plurality of projection signals $p_{new}(r, t)$ for each backprojection position.

4. The method of claim 1, wherein the plurality of acoustic signals produced by the plurality of light beams are detected by a plurality of detectors.

5. The method of claim 1, wherein the plurality of light beams comprise short laser pulses.

6. The method of claim 1, comprising providing the reconstructed image for rendering.

7. The method of claim 1, wherein the detector is one of a plurality of acoustic detectors configured to detect the plurality of acoustic signals.

8. The method of 7, wherein the plurality of acoustic detectors convert an acoustic wave to a plurality of time dependent electrical signals.

9. The method of claim 1, wherein a cutoff frequency of the weighted ramp filter is based upon the weighting function.

10. The method of claim 1, wherein the source is a short pulse laser.

11. The method of claim 2, wherein the plurality of measurement signals p(k) are determined by Fourier transformation of a plurality of time-dependent electrical signals corresponding to a plurality of acoustic signals detected with the detector.

12. The method of claim 3, wherein generating the reconstructed image of the object by FBP further comprises transferring accumulated signal values for each backprojection position to grey scale values for rendering of the image.

* * * * *